United States Patent
Jeon et al.

(10) Patent No.: US 9,316,616 B2
(45) Date of Patent: Apr. 19, 2016

(54) METHOD OF DETERMINING OR ESTIMATING NUCLEOTIDE SEQUENCE OF NUCLEIC ACID

(71) Applicant: Samsung Electronics Co., Ltd., Suwon-si, Gyeonggi-do (KR)

(72) Inventors: Tae-han Jeon, Hwaseong-si (KR); Dong-ho Lee, Seongnam-si (KR); Hee-jeong Jeong, Seoul (KR); Jeo-young Shim, Yongin-si (KR); Kun-sun Eom, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 556 days.

(21) Appl. No.: 13/773,328

(22) Filed: Feb. 21, 2013

(65) Prior Publication Data

US 2014/0008225 A1    Jan. 9, 2014

(30) Foreign Application Priority Data

Jul. 3, 2012 (KR) .................. 10-2012-0072406

(51) Int. Cl.
| | |
|---|---|
| *B82Y 5/00* | (2011.01) |
| *G01N 27/447* | (2006.01) |
| *G01N 33/487* | (2006.01) |
| *B82Y 15/00* | (2011.01) |

(52) U.S. Cl.
CPC ..... *G01N 27/44791* (2013.01); *G01N 33/48721* (2013.01); *B82Y 5/00* (2013.01); *B82Y 15/00* (2013.01); *Y10S 977/924* (2013.01)

(58) Field of Classification Search
CPC .. C12Q 1/6869; C12Q 1/6816; C12Q 1/6825; C12Q 1/6827; C12Q 1/6874; C12Q 2565/631; C12Q 2565/607; C12Q 2565/629; G01N 33/48721; B82Y 15/00; B82Y 30/00; Y10S 977/953

See application file for complete search history.

(56) References Cited

U.S. PATENT DOCUMENTS

| | | | |
|---|---|---|---|
| 6,362,002 B1 | 3/2002 | Denison et al. | |
| 6,905,586 B2 | 6/2005 | Lee et al. | |
| 7,279,337 B2 | 10/2007 | Zhu | |
| 7,556,922 B2 | 7/2009 | Block et al. | |
| 8,092,697 B2 | 1/2012 | Branton et al. | |
| 2011/0214991 A1* | 9/2011 | Kim ................. | G01N 27/453 204/452 |

FOREIGN PATENT DOCUMENTS

WO    WO 2007/013370 A1    2/2007

OTHER PUBLICATIONS

Manrao et al., "Reading DNA at single-nucleotide resolution with a mutant MspA nanopore and phi29 DNA polymerase," *Nature Biotechnology*, 30(4): 349-354 (2012).

Venkatesan et al., "Stacked Graphene-$Al_2O_3$ Nanopore Sensors for Sensitive Detection of DNA and DNA Protein Complexes," *ACSNANO*, 6(1): 441-450 (2012).

\* cited by examiner

*Primary Examiner* — J. Christopher Ball
(74) *Attorney, Agent, or Firm* — Leydig, Voit & Mayer, Ltd.

(57) ABSTRACT

A method of determining or estimating a nucleotide sequence of a nucleic acid by using a device with a nanopore.

19 Claims, 2 Drawing Sheets

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic (20mer sample polynucleotide)

<400> SEQUENCE: 1
ataactgtac tagcttcagg                                                  20
```

METHOD OF DETERMINING OR ESTIMATING NUCLEOTIDE SEQUENCE OF NUCLEIC ACID

CROSS-REFERENCE TO RELATED APPLICATIONS

This application claims the benefit of Korean Patent Application No. 10-2012-0072406, filed on Jul. 3, 2012, in the Korean Intellectual Property Office, the entire disclosure of which is incorporated herein in by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 499 Byte ASCII (Text) file named "711820_ST25.txt," created on Feb. 21, 2013.

BACKGROUND

1. Field

The present disclosure relates to methods of determining or estimating a nucleotide sequence of a nucleic acid using a device including a nanopore.

2. Description of the Related Art

Methods using a nanogap have been researched for DNA detection systems imitating biopores, in which, for example, a tunneling current or a blokade current may be measured while DNA or RNA passes through the nanogap. However, there remains a demand for new methods of analyzing a nucleotide sequence of a nucleic acid.

SUMMARY

Provided are efficient methods for determining or estimating a nucleotide sequence of a nucleic acid. In one embodiment, the method comprises translocating a nucleic acid through a nanopore (e.g., from one end of a nanopore to an opposite end of the nanopore), wherein the nanopore comprises first and second electrodes disposed on an inner wall of the nanopore positioned to apply a voltage across the diameter of the nanopore, and each electrode has a terminal defining at least a portion of the inner wall of the nanopore with a thickness sufficient to detect a signal corresponding to at least two consecutive nucleotides at once; measuring an electrical signal between the first and second electrodes as the nucleic acid translocates through the nanopore, wherein the electrical signal is measured with respect to nucleic acid translocating time; dividing the obtained electrical signal into segments that correspond to the number of nucleotides detected according to the thickness of the electrodes; comparing the measured electrical signal of each segment with the electrical signal of a segment of a control to determine the nucleotide composition corresponding to the electrical signal of each segment; and determining or estimating the nucleotide sequence of the nucleic acid based on the nucleotide composition of each segment.

In another aspect, the method of determining or estimating a nucleotide sequence of a nucleic acid comprises translocating the nucleic acid from one end of a nanopore to an opposite end thereof, wherein the nanopore has a length longer than at least one consecutive nucleotides and able to be blocked in a lengthwise direction by at least two consecutive nucleotides, and a first electrode and a second electrode positioned to apply a voltage across the length of the nanopore; applying a voltage across the length of the nanopore, from one end to the opposite end thereof; measuring an electrical signal between the first and second electrodes as the nucleic acid translocates through the nanopore with respect to nucleic acid translocating time; dividing the obtained electrical signal into segment that correspond to the number of nucleotides detected according to the length of the nanopore; comparing the measured electrical signal of each segment with the electrical signal of a segment from a control to determine a nucleotide composition corresponding to the electrical signal of each segment; and determining the nucleotide sequence of the nucleic acid based on the nucleotide composition of each segment.

Also provided is a device useful for determining a nucleotide sequence. In one aspect, the device comprises a substrate; a nanopore passing through the thickness of the substrate; first and second electrodes disposed on an inner wall of the nanopore positioned to apply a voltage across the diameter of the nanopore, wherein each electrode has a terminal defining at least a portion of the inner wall of the nanopore with a thickness sufficient to detect a signal corresponding to at least two consecutive nucleotides at once; a voltage source electrically connected to at least one of the first or second electrode; and an electrical signal measuring device electrically connected to at least one of the first or second electrode.

In another aspect, the device comprises a substrate comprising a nanopore passing through a thickness of the substrate, the nanopore having a length longer than at least one consecutive nucleotides of a nucleic acid molecule; a first electrode and a second electrode disposed to apply a voltage through the length of the nanopore; a voltage source electrically connected to at least one of the first and second electrodes; and an electrical signal measuring device electrically connected to at least one of the first and second electrodes.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Provided is a method for analyzing a nucleic acid comprising translocating a nucleic acid through a nanopore (e.g., from one end of a nanopore to an opposite end of the nanopore), wherein the nanopore comprises first and second electrodes disposed on an inner wall of the nanopore positioned to apply a voltage across the diameter of the nanopore, and each electrode has a terminal defining at least a portion of the inner wall of the nanopore with a thickness sufficient to detect a signal corresponding to at least two consecutive nucleotides at once; measuring an electrical signal between the first and second electrodes as the nucleic acid translocates through the nanopore, wherein the electrical signal is measured with respect to nucleic acid translocating time; dividing the obtained electrical signal into segments that correspond to the number of nucleotides detected according to the thickness of the electrodes; comparing the measured electrical signal of each segment with the electrical signal of a segment of a control to determine the nucleotide composition corresponding to the electrical signal of each segment; and determining or estimating the nucleotide sequence of the nucleic acid based on the nucleotide composition of each segment.

The nanopore may be part of a nucleotide sequence analysis device comprising a substrate including the nanopore passing through a thickness thereof; a voltage source electrically connected to at least one of the first or second electrode; and an electrical signal measuring device electrically connected to at least one of the first or second electrode.

Thus, the nucleotide sequence determination or estimation method may include translocating nucleotides from one end of the nanopore to the opposite end of the nanopore in the nucleic acid analysis device, the nucleic acid analysis device including a substrate having a nanopore passing through a thickness of the substrate; an electrode, including first and second electrodes disposed on an inner wall of the nanopore to apply a voltage across the nanopore and each having a terminal defining the inner wall of the nanopore with a thickness sufficient to ensure detection of at least two consecutive nucleotides at once; a voltage source electrically connected to the electrode; and an electrical signal measuring device electrically connected to the electrode.

In a related aspect, there is provided a method of determining or estimating a nucleotide sequence of a nucleic acid, the method including translocating the nucleic acid through a nanopore (e.g., from one end of a nanopore to an opposite end of the nanopore), wherein the nanopore is part of a nucleic acid analysis device that includes a substrate having a nanopore passing through a thickness of the substrate; an electrode, including first and second electrodes disposed on an inner wall of the nanopore to apply a voltage across the nanopore and each having a terminal defining the inner wall of the nanopore with a thickness sufficient to ensure detection of at least two consecutive nucleotides at once; a voltage source electrically connected to the electrode; and an electrical signal measuring device electrically connected to the electrode; measuring an electrical signal with respect to nucleic acid translocating time using the electrical signal measuring device; dividing the electrical signal into segments that correspond to the number of nucleotides detected according to the thickness of the electrodes; comparing an electrical signal of each segment with an electrical signal of each segment of a control group having a known nucleotide sequence to determine a nucleotide composition corresponding to the electrical signal of each segment; and determining or estimating the nucleotide sequence of the nucleic acid based on the nucleotide composition of each segment.

The nucleic acid analysis device may further include a cis chamber for accommodating a liquid in fluid communication with one end of the nanopore; and a trans chamber for accommodating a liquid in fluid communication with the opposite end of the nanopore. These chambers may have any form able to contain liquid. For example, the cis and trans chambers may be sealed with an opening controllable to be closed or open, or may be open in at least one direction.

The nanopore may include a fluid flowable path, which may be a channel having closed periphery or may be a gap with partially open periphery. In other words, the nanopore may be defined by two ends or openings (e.g., generally openings in two surfaces on opposite sides of a substrate) and a channel forming a fluid-flowable path penetrating the substrate and connecting the two openings. The two opposite ends of the nanopore may be linked together by a path or channel that is linear or curved. The substrate may be a solid substrate able to support fluid flow through the channel.

The substrate may be derived from a non-biological material, rather than from a biological material like a biological membrane. The substrate may be an insulating material, for instance, silicon nitride ($Si_3N_4$), aluminum ($Al_2O_3$), silica ($SiO_2$), a plastic such as polytetrafluoroethylene (PTFE), an elastomer such as a curable bicomponent silicon rubber, or a combination thereof. The substrate may have a flat form, for example, a film or membrane form, or an irregular form. In some embodiments, at least a region of the substrate contacting the first end of the nanopore may be flat, at least a portion of one side of the substrate in which the nanopore is formed is substantially flat. The substrate may have a layered structure, and in some embodiments, may have a layered structure with a thin membrane like a silicon membrane supported by a support material. A local thickness of the substrate with the nanopore disposed may be from about 0.34 nm to about 1000 nm, and in some embodiments, may be from about 0.34 nm to about 500 nm, and in some other embodiments, may be from about 1 nm to about 50 nm.

A cross-sectional length of the nanopore may be from about 1 nm to about 100 nm, and in some embodiments, may be from about 1 nm to about 5 nm, and in some other embodiments, may be from about 1 nm to about 10 nm, and in some still other embodiments, may be from about 5 nm to about 10 nm, and in some yet other embodiments, may be from about 1 nm to about 25 nm. The nanopore may have a circular or polygonal cross-section. When the nanopore has a circular cross-section, the cross-sectional length of the nanopore indicates a diameter of the nanopore. When the nanopore has a polygonal cross-sectional, the cross-sectional length indicates the shortest distance. The cross-sectional length of the nanopore may be consistent in a longitudinal direction of the nanopore.

A length of the nanopore in the longitudinal direction may be not specifically limited provided that it allows nucleotide to pass through. The length of the nanopore in the longitudinal direction may be shorter than a length of the nucleic acid to be passed. The length of the nanopore in the longitudinal direction may be same or larger than a distance between nucleotides of a nucleic acid molecule. Thus, the nanopore may have a length, for example, from about 0.34 nm to about 500 nm, about 0.68 nm to about 500 nm, about 1.02 nm to about 500 nm or about 1.36 nm to about 500 nm. Alternatively, the length of the nanopore, which may be shorter than a distance between nucleotides of a nucleic acid molecule, may be, for example, about 0.34 nm or less.

The device may include a first electrode and the second electrode disposed or positioned to contact an internal space of the nanopore. For instance, the electrodes may define at least a portion of the inner wall of the nanopore, or may have terminal contacts that define a least a portion of the inner wall of the nanopore. The first electrode and the second electrode as a pair may be electrically connected to a voltage source and/or an electrical signal measuring device. In some embodiments, multiple pairs of the first and second electrodes may be disposed or positioned in the nanopore in this manner, and separated from each other by an insulating material. The first electrode and the second electrode may be disposed in a vertical direction with an insulating material therebetween insulating one from another.

The electrical signal measuring device connected to at least one of the first or second electrodes (or between the first and second electrode) may be a device for measuring a current, a voltage, an impedance, an electric capacity, or a combination thereof.

The nucleic acid analysis device may further include an electrode disposed at, on, or in proximity to the first end of the nanopore, and an electrode disposed at, on, or in proximity to the opposite end of the nanopore (e.g., third and forth electrodes). In other words, the nucleic acid device may have electrodes positioned to apply a voltage across the length of the nanopore. The electrodes may be electrically connected to the voltage source and/or the electrical signal measuring device.

The nucleic acid analysis device may further include a unit for linearly translocating nucleic acids to pass through the nanopore. This unit may provide a concentration gradient, a voltage gradient, a magnetic force gradient between the first end and the opposite end of the nanopore, or a combination thereof. The unit may include at least two electrodes disposed between the first end and the opposite end of the nanopore, or in a channel. These electrodes may define at least a part of the nanopore, or may be separate from the nanopore. Thus, for instance, the electrodes may be disposed outside of the nanopore, positioned opposite each other relative to the nanopore. When the electrodes define at least part of the nanopore, the at least part of the nanopore may be formed of a conductive material. In some embodiments, at least part of the nanopore may be coated or embedded with a conductive material. The unit for linear movement of nucleic acids may be at least one selected from the group consisting of a molecular motor, a mechanical driving apparatus, or a combination thereof that are disposed between the first end and the opposite end of the nanopore or are disposed in a channel. These apparatuses may include a power supply electrically connected thereto.

Terminals of the first and second electrodes may have a thickness enough to sense at least two consecutive nucleotides. The phrase "at least two consecutive nucleotides" includes one nucleotide and at least a part of the one or more consecutive nucleotides. Thickness, in this regard, means a dimension in a direction parallel to the length of the nanopore. The thickness may be greater than about 0.34 nm. For example, the thickness may be from greater than about 0.34 nm to less than 0.68 nm, and in some embodiments, may be from greater than about 0.68 nm to less than about 1.02 nm, and in some other embodiments, may be from greater than about 1.02 nm to less than about 1.36 nm.

The translocating of the nucleic acids may be achieved by an arbitrary driving force applied to the nucleic acid between the first and opposite ends of the nanopore. The translocating of the nucleic acids may be implemented by applying at least one driving force selected from the group consisting of natural gravity, diffusion, a voltage gradient, a magnetic force gradient, a molecular motor, a mechanical force, and a combination thereof. In one embodiment, the translocating of the nucleic acids may be achieved by applying a voltage gradient between the first end and the opposite end of the nanopore. In this regard, the first end and the opposite end of the nanopore may be contacted with an electrolyte solution. The electrolyte solution may be a solution including, for example, KCl, NaCl, or a combination thereof. The nucleic acid may be selected from among DNA, RNA, or a combination thereof. The nucleic acid may have a form selected from among a single strand, a double strand, and a combination thereof. The nucleic acid may have a secondary structure or a tertiary structure. The nucleic acid may be in an isolated form from other polymer molecules.

The nucleotide sequence determination or estimation method may include measuring an electrical signal with respect to nucleic acid translocating time (e.g., as a function of, or plotted against, translocation time) by using the electrical signal measuring device. The electrical signal may be a current, a voltage, an impedance, an electric capacity, or a combination thereof. The measuring of the electrical signal may include measuring a tunneling current. In the measuring of the electrical signal, an electrical signal detected from an identical nucleotide composition at once may be the same. For example, with the assumption that the electrical signal measuring device is able to measure two consecutive nucleotides at once, for example, AT and TA, electrical signals detected from the two nucleotides may be the same because of the same nucleotide composition, even with the different sequences of the consecutive nucleotides. For example, if the electrical signal measuring device is able to detect three consecutive nucleotides at once, for example, AAT, ATA, and TAA, electrical signals detected from the three consecutive nucleotides may be the same because of the same nucleotide composition, even with the different sequences of the consecutive nucleotides.

The nucleotide sequence determination or estimation method may include dividing the obtained electrical signal into segment that corresponds to the number of nucleotides detected according to the thickness of the electrodes at any given point in time. The segment may correspond to an electrical signals corresponding to the at least two consecutive unit nucleotides detected at any given point in time. As used herein, the terms "nucleotide" and "base" are interchangeable. The phrase "the number of nucleotides detected according to the thickness of the electrodes" refers to the number of nucleotides the electrical signal measuring device is able to measure at once due to a limited area of the first electrode and a limited contact area of the first electrode to the nucleic acid. If the electrical signal measuring device is able to measure an electrical signal from two, three, or four unit nucleotides at once, this indicates that the segment corresponds to an electrical signal from 2, 3, or 4 consecutive nucleotides. The number of nucleotides detected according to the thickness of the electrode may be from 2 to 10, and in some embodiments, may be from 2 to 6, and in some other embodiments, may be from 2 to 4. The dividing of the electrical signal may involve determining the time taken to move one nucleotide and multiplying the time by the number of nucleotides detected according to the thickness of the electrode to obtain an electrical signal segment for the numbers of nucleotides. The translocation time for one nucleotide may be obtained by dividing the translocation time for a nucleic acid with the number of nucleotide thereof. The dividing of the electrical signal may be performed with a time interval corresponding to one nucleotide translocation time.

The nucleotide sequence determination or estimation method may include comparing an electrical signal of each segment with that of a segment originating from a control group having a known nucleotide sequence to determine a nucleotide composition corresponding to the electrical signal of each segment. For instance, a nucleic acid with a known sequence can be translocated through the device, and the electrical signal measured from the device as the nucleic acid translocates through the nanopore, plotted against translocation time, is used as a control to determine the electrical signal characteristics (e.g., signal strength) that correspond to a give nucleotide unit composition.

The electrical signal divided into segments provides signals for overlapping segments of the nucleic acid, as illustrated in the Figures. The nucleotide sequence determination or estimation method may include determining or estimating the nucleotide sequence of the nucleic acid based on the nucleotide composition of each segment. The step of determining or estimating may comprise, arranging each segment (S) in the order of translocating time as $S1, S2, S3, \ldots, St, St+1, St+2, St+3, \ldots$; providing each potential sequence of each segment (S) from the composition; aligning ith-nth sequence of each potential sequence of a segment St with the $1^{st}$-(n−j)th sequence of each potential sequence of a segment St+j, wherein j is an integer from 1 to n−1, wherein i is j+1 and an integer from 2 to n, wherein n refers to the number of nucleotides detected according to the thickness of the electrode; determining or estimating the sequence of a segment St as being one more potential sequences that are identical with the aligned $1^{St}$-(n−j)th sequence of each potential sequence of a segment St+j; and determining or estimating the nucleotide sequence of the nucleic acid by reading the sequence of each segment in the order of translocating time. The each segment may be arranged in the order of a time interval corresponding to one nucleotide (herein after "single nucleotide shift"). For example, with the assumption that an electrical signal of a first nucleotide composition AAT (also identical to the electrical signal of ATA or TAA) is obtained with a single nucleotide shift, an electrical signal of a second nucleotide composition AAT (also identical to the electrical signal of ATA or TAA) is obtained with a further single nucleotide shift, and an electrical signal of a third nucleotide composition AAC (also identical to the electrical signal of ACA or CAA) is obtained from a further single nucleotide shift, second and third single nucleotide sequences of the first nucleotide composition (AAT, ATA, or TAA) should overlap with first and second single nucleotide sequences of the second nucleotide composition (AAT, ATA, or TAA), and second and third single nucleotide sequences of the second nucleotide composition (AAT, ATA, or TAA) should overlap with first and second single nucleotide sequences of the third nucleotide composition (AAC, ACA, or CAA). First, second, and third single nucleotide sequences satisfying these requirements are ATA.

The nucleotide sequence determination or estimation method may include recording the above-described dividing operation, comparing operation, and determining operation in a computer readable medium. The above-described nucleic acid analysis device may include a computer readable recording medium storing the above-described information and or a program or instructions for conducting the dividing operation, comparing operation, and determining operation. The dividing operation, the comparing operation, and the determining operation may be executable by a computer.

In another aspect, the method of determining or estimating a nucleotide sequence of a nucleic acid comprises translocating the nucleic acid from one end of a nanopore to an opposite end thereof, wherein the nanopore has a length longer than at least one consecutive nucleotides and able to be blocked in a lengthwise direction by at least two consecutive nucleotides, and a first electrode and a second electrode positioned to apply a voltage across the length of the nanopore; applying a voltage across the length of the nanopore, from one end to the opposite end thereof; measuring an electrical signal between the first and second electrodes as the nucleic acid translocates through the nanopore with respect to nucleic acid translocating time; dividing the obtained electrical signal into segments that correspond to the number of nucleotides detected according to the length of the nanopore; comparing the measured electrical signal of each segment with the electrical signal of a segment from a control to determine a nucleotide composition corresponding to the electrical signal of each segment; and determining or estimating the nucleotide sequence of the nucleic acid based on the nucleotide composition of each segment.

The nanopore may be part of a nucleic acid analysis device comprising a substrate including the nanopore passing through a thickness of the substrate; a first electrode and a second electrode positioned to apply a voltage across the length of the nanopore; a voltage source electrically connected to the first and second electrodes; and an electrical signal measuring device electrically connected to the first and second electrodes.

Thus, according to another aspect, there is provided a method of determining or estimating a nucleotide sequence of a nucleic acid, the method including translocating the nucleic acid from an end of a nanopore of a nucleic acid analysis device to an opposite end of the nanopore, wherein the nucleic acid analysis device includes a substrate having a nanopore passing through a thickness of the substrate, the nanopore having a length longer than at least one consecutive nucleotides and thus being able to be blocked in a lengthwise direction by the same; a first electrode and a second electrode disposed to apply a voltage through the length of the nanopore; a voltage source electrically connected to the first and second electrodes; and an electrical signal measuring device electrically connected to the first and second electrodes; measuring an electrical signal with respect to nucleic acid translocating time using the electrical signal measuring device; dividing the electrical signal into segments that correspond to the number of nucleotides detected according to the length of the nanopore; comparing an electrical signal of each segment with an electrical signal of each segment of a control group having a known nucleotide sequence to determine a nucleotide composition corresponding to the electrical signal of each segment; and determining or estimating the nucleotide sequence of the nucleic acid based on the nucleotide composition of each segment.

The nucleotide sequence determination or estimation method may include translocating nucleotides from one end of the nanopore to the opposite end of the nanopore in the nucleic acid analysis device, including a substrate with the nanopore passing through a thickness of the substrate, the nanopore having a length longer than at least one consecutive nucleotides and thus being able to be blocked in a lengthwise direction by at least two consecutive nucleotides; a first electrode and a second electrode disposed to apply a voltage through the length of the nanopore; a voltage source electrically connected to the first and second electrodes; and an electrical signal measuring device electrically connected to the first and second electrodes.

In the nucleotide sequence method, the nucleic acid analysis device may include a substrate including the nanopore passing through a thickness of the substrate, the nanopore having a length longer than at least one consecutive nucleotides and thus able to be blocked in a lengthwise direction by at least two consecutive nucleotides. The nanopore may have a length that may be blocked by at least two consecutive nucleotides, for example, two, three, or four consecutive nucleotides. The length of the nanopore may be greater than about 0.34 nm. For example, the length of the nanopore may be from greater than about 0.34 nm to less than about 0.68 nm, and in some other embodiments, may be from greater than about 0.68 nm to less than about 1.02 nm, and in some other embodiments, may be from greater than about 1.02 nm to less than about 1.36 nm.

The nucleic acid analysis device used in the nucleotide sequence determination or estimation method includes a first electrode and a second electrode, which are disposed to apply a voltage across the length of the nanopore. The first electrode may be disposed at, in, or on a first end of the nanopore, and the fourth electrode may be disposed at, in, or on an end of the nanopore opposite to the first end. The first electrode and the second electrode may be electrically connected to the voltage source and the electrical signal measuring device.

The nanopore may have a length enough to block at least two consecutive nucleotides. The phrase "at least two consecutive nucleotides" includes one nucleotide and at least a part of the one or more consecutive nucleotides. The length may be greater than about 0.34 nm. For example, the length may be from greater than about 0.34 nm to less than 0.68 nm, and in some embodiments, may be from greater than about 0.68 nm to less than about 1.02 nm, and in some other embodiments, may be from greater than about 1.02 nm to less than about 1.36 nm.

The nucleotide sequence determination or estimation method may include measuring an electrical signal with respect to nucleic acid translocating time (e.g., as a function of, or plotted against, translocation time) by using the electrical signal measuring device. The electrical signal may be a current, a voltage, an impedance, an electric capacity, or a combination thereof. The measuring of the electrical signal may include measuring a blockade current. In the measuring of the electrical signal, an electrical signal detected from an identical nucleotide composition at once may be the same. For example, with the assumption that the electrical signal measuring device is able to measure two consecutive nucleotides at once, for example, AT and TA, electrical signals detected from the two nucleotides may be the same because of the same nucleotide composition, even with the different sequences of the consecutive nucleotides. For example, if the electrical signal measuring device is able to detect three consecutive nucleotides at once, for example, AAT, ATA, and TAA, electrical signals detected from the three consecutive nucleotides may be the same because of the same nucleotide composition, even with the different sequences of the consecutive nucleotides.

The nucleotide sequence determination or estimation method may include dividing the obtained electrical signal into segment that corresponds to the number of nucleotides detected according to the length of the nanopore at any given point in time. The segment may correspond to an electrical signals corresponding to the at least two consecutive unit nucleotides detected at any given point in time. As used herein, the terms "nucleotide" and "base" are interchangeable. The phrase "the number of nucleotides detected according to the length of the nanopore" refers to the number of nucleotides that the electrical signal measuring device is able to measure at once due to a limited blocking of the nucleic acid by the limited length of the nanopore. If the electrical signal measuring device is able to measure an electrical signal from two, three, or four unit nucleotides at once, this indicates that the segment corresponds to an electrical signal from 2, 3, or 4 consecutive nucleotides. The number of nucleotides detected according to the length of the nanopore may be from 2 to 10, and in some embodiments, may be from 2 to 6, and in some other embodiments, may be from 2 to 4. The dividing of the electrical signal may involve determining the time taken to move one nucleotide and multiplying the time by the number of nucleotides detected according to the length of the nanopore to obtain an electrical signal segment for the numbers of nucleotides. The translocation time for one nucleotide may be obtained by dividing the translocation time for a nucleic acid with the number of nucleotide thereof. The dividing of the electrical signal may be performed with a time interval corresponding to one nucleotide translocation time.

The nucleotide sequence determination or estimation method may include comparing an electrical signal of each segment with that of a segment originating from a control group having a known nucleotide sequence to determine a nucleotide composition corresponding to the electrical signal of each segment. For instance, a nucleic acid with a known sequence can be translocated through the device, and the electrical signal measured from the device as the nucleic acid translocates through the nanopore, plotted against translocation time, is used as a control to determine the electrical signal characteristics (e.g., signal strength) that correspond to a give nucleotide unit composition.

The electrical signal divided into segments provides signals for overlapping segments of the nucleic acid, as illustrated in the Figures. The nucleotide sequence determination or estimation method may include determining or estimating the nucleotide sequence of the nucleic acid based on the nucleotide composition of each segment. The step of determining or estimating may comprise, arranging each segment (S) in the order of translocating time as S1, S2, S3, . . . , St, St+1, St+2, St+3, . . . ; providing each potential sequence of each segment (S) from the composition; aligning ith-nth sequence of each potential sequence of a segment St with the $1^{st}$-(n−j)th sequence of each potential sequence of a segment St+j, wherein j is an integer from 1 to n−1, wherein i is j+1 and an integer from 2 to n, wherein n refers to the number of nucleotides detected according to the length of the nanopore; determining or estimating the sequence of a segment St as being one more potential sequences that are identical with the aligned $1^{st}$-(n−j)th sequence of each potential sequence of a segment St+j; and determining or estimating the nucleotide sequence of the nucleic acid by reading the sequence of each segment in the order of translocating time. The each segment may be arranged in the order of a time interval corresponding to one nucleotide (herein after "single nucleotide shift"). For example, with the assumption that an electrical signal of a first nucleotide composition AAT (also identical to the electrical signal of ATA or TAA) is obtained with a single nucleotide shift, an electrical signal of a second nucleotide composition AAT (also identical to the electrical signal of ATA or TAA) is obtained with a further single nucleotide shift, and an electrical signal of a third nucleotide composition AAC (also identical to the electrical signal of ACA or CAA) is obtained from a further single nucleotide shift, second and third single nucleotide sequences of the first nucleotide composition (AAT, ATA, or TAA) should overlap with first and second single nucleotide sequences of the second nucleotide composition (AAT, ATA, or TAA), and second and third single nucleotide sequences of the second nucleotide composition (AAT, ATA, or TAA) should overlap with first and second single nucleotide sequences of the third nucleotide composition (AAC, ACA, or CAA). First, second, and third single nucleotide sequences satisfying these requirements are ATA.

The nucleic acid analysis device may further include a unit for linearly translocating nucleic acids to pass through the nanopore, as previously described. All other aspects of the nucleotide sequence determination or estimation method and device used in same are as previously described.

The above-described nucleic acid analysis device may include a computer readable recording medium for storing the above-described information. The dividing operation, the comparing operation, and the arranging operation may be executable by a computer.

Also provided is a device useful for determining a nucleotide sequence. In one aspect, the device comprises a substrate; a nanopore passing through the thickness of the substrate; first and second electrodes disposed on an inner wall of the nanopore positioned to apply a voltage across the diameter of the nanopore, wherein each electrode has a terminal defining at least a portion of the inner wall of the nanopore with a thickness sufficient to detect a signal corresponding to at least two consecutive nucleotides at once; a voltage source electrically connected to at least one of the first or second electrode; and an electrical signal measuring device electrically connected to at least one of the first or second electrode.

In another aspect, the device comprises a substrate comprising a nanopore passing through a thickness of the substrate, the nanopore having a length equivalent to at least two consecutive nucleotides of a nucleic acid molecule; a first electrode and a second electrode disposed to apply a voltage through the length of the nanopore; a voltage source electrically connected to at least one of the first and second electrodes; and an electrical signal measuring device electrically connected to at least one of the first and second electrodes.

All other aspects of the device are as described with respect to the disclosed methods of determining a nucleotide sequence.

The present invention will be described in further detail with reference to the following examples. These examples are for illustrative purposes only and are not intended to limit the scope of the invention.

Example 1

Figure 1:
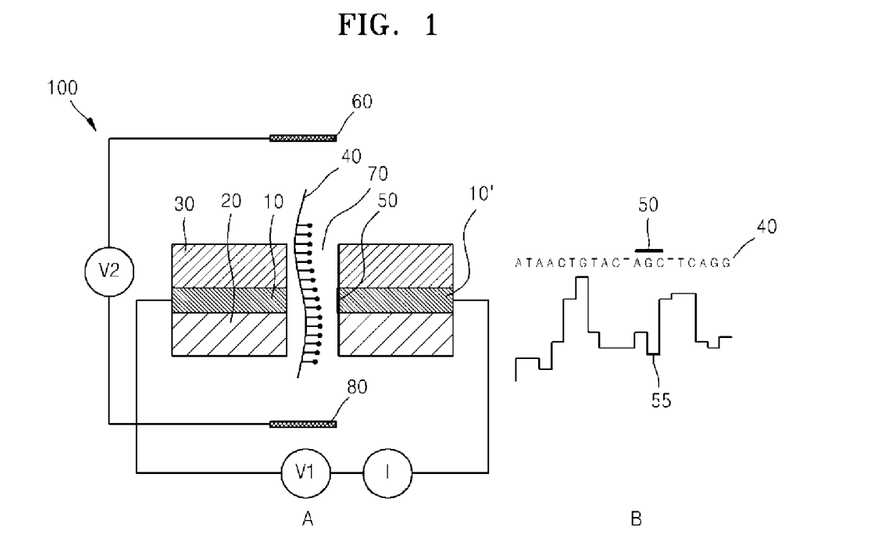
FIG. 1 is a schematic view of a nucleic acid analysis device for determining a nucleotide sequence of a nucleic acid.

Nucleotide Sequence Determination Method by Measuring Electrical Signals of at Least Two Consecutive Nucleotides at Once (1) Nucleotide Analysis Device Including Nanopore FIG. 1 is a schematic view of a nucleic acid analysis device 100 for determining a nucleotide sequence of a nucleic acid, which may be used in a method, according to an embodiment of the present disclosure.

Referring to FIG. 1A, the nucleotide sequence analysis device 100 may include substrates 20, and 30, each including a nanopore passing through a thickness of the substrate; a first electrode 10 and a second electrode 10' disposed on an inner wall of the nanopore to apply a voltage across the nanopore and each having a terminal 50 defining the inner wall of the nanopore with a thickness enough to ensure detection of at least two consecutive nucleotides at once; a voltage source V1 electrically connected to the first electrode 10 and the second electrode 10; and an electrical signal measuring device I electrically connected to the first electrode 10 and the second electrode 10'. The first electrode 10 and the second electrode 10' in the nanopore 70 may be disposed on an insulating material 20, with an insulating material 30 covering the first electrode 10 and the second electrode 10'. Nucleic acid 40 in FIG. 1A is shown able to pass through nanopore 70. The terminals 50 of the first and second electrodes 10 and 10' for applying a voltage to fluid flowing through the nanopore may have a thickness enough to sense at least two consecutive nucleotides. The thickness of each electrode terminal 50 may be, for example, about 1.02 nm.

FIG. 1B illustrates a result from an electrical signal division by a unit nucleotide number of at least two, for example, three consecutive nucleotides.

The result of FIG. 1B may be attainable by shifting the nucleic acid 40 from an end of the nanopore to the opposite end of the nanopore in the nucleotide analysis device; measuring an electrical signal with respect to nucleic acid translocating time using the electrical signal measuring device; and dividing the electrical signal into segments that correspond to the number of nucleotides detected according to the thickness of the electrodes. The segment may correspond to the unit nucleotide number of at least two, for example, three consecutive nucleotides. The electrical signal segments that correspond to the number of nucleotides detected according to the thickness of the electrodes may be obtained by dividing the electrical signal with a time interval taken to translocate the number of nucleotides detected according to the thickness of the electrodes. For example, nucleic acid 40 is shown to contain nucleotide sequence AGC currently being sensed through electrode 50, and the electrical signal corresponding to this example nucleotide sequence is labeled as segment 55 on the electrical signal plot. The nucleotide composition of the segment may be obtained by comparing the segment with those from an electrical signal of a nucleic acid with a known sequence.

Figure 2:
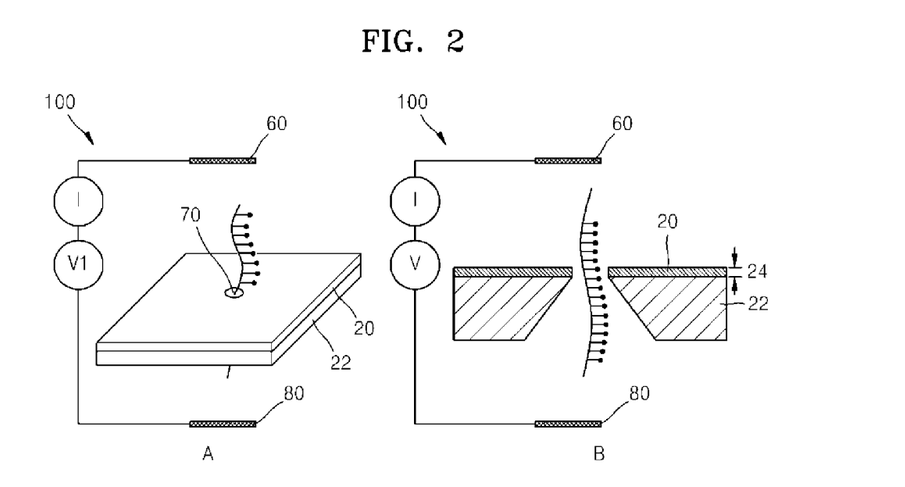
FIG. 2 is a schematic view of a nucleic acid analysis device for determining a nucleotide sequence of a nucleic acid.

FIG. 2 is a schematic view of a nucleic acid analysis device 100 for determining a nucleotide sequence of a nucleic acid, which may be used in a method, according to another embodiment of the present disclosure. FIGS. 2A and 2B are a perspective view and a cross-sectional side view of the nucleic acid analysis device 100, respectively.

Referring to FIG. 2, the nucleotide analysis device 100 may include a substrate 20 including a nanopore 70 passing through a thickness of the substrate 20 and having a length 24 longer than at least one consecutive nucleotides and thus being able to be blocked in a lengthwise direction by at least two consecutive nucleotides; a third electrode 60 and a fourth electrode 80 disposed to apply a voltage through the length of the nanopore 70; a voltage source (V) electrically connected to the third and fourth electrodes 60 and 80; and an electrical signal measuring device (I) electrically connected to the third electrode 60 and the fourth electrode 80. In FIG. 2, substrate 20 is shown as a thin membrane placed on support material 22.

(2) Nucleotide Sequence Determination

The nucleotide sequence analysis device of FIG. 1 was used to determine a nucleotide sequence.

In the nucleotide sequence analysis device used in this test, the end of the electrodes defining the inner wall thereof may have a thickness of about of 1.02 nm, which was enough to sense at least two consecutive nucleotides at once. The nucleic acid analysis device may include a cis chamber for accommodating a liquid in fluid communication with one end of the nanopore; and a trans chamber for accommodating a liquid in fluid communication with the opposite end of the nanopore. The cis/trans chamber was filled with a 1M KCl solution for DNA translocation and signal measurement. To remove migration speed or noise, the cis and trans chambers disposed upon one another may be filled with different concentration. A voltage of about 200 mV to about 300 mV was applied to the third electrode 60 and the fourth electrode 80 as a driving force for DNA migration. An Ag electrode and an AgCl electrode were used as the third and fourth electrodes 60 and 80, respectively.

A polynucleotide including 20 nucleotides having a SEQ ID No. 1 was added to the cis chamber, and a voltage was applied through the third electrode 60 and the fourth electrode 80 to migrate the polynucleotide from the cis chamber to the trans chamber. In particular, the polynucleotide was migrated from one end to the opposite end of the nanopore in the nucleotide analysis device. During translocation, an electrical signal with respect to time using the electrical signal measuring device was measured. Thereafter, the signal was analyzed by dividing the electrical signal into a segment of three consecutive nucleotides; comparing an electrical signal of each segment with an electrical signal of each segment of a control group having a known nucleotide sequence to determine a nucleotide composition corresponding to the electrical signal of each segment; and determining or estimating the nucleotide sequence of the nucleic acid based on the nucleotide composition of each segment.

As a result of measuring electrical signals with respect to nucleic acid translocating time using the electrical signal measuring device, the same electrical signal was detected from each unit nucleotide number of the three consecutive nucleotides with the same nucleotide composition. For example, the same electrical signal was obtained from unit nucleotides having the same composition of, for example, AAT, ATA, and TAA, or ACT, ATC, CAT, CTA, TAC, and TCA.

In this regard, when using an electrical signal determining device able to measure an electrical signal of n number of nucleotides at once, the number of electrical signals detected from each unit nucleotide sequence may be equal to the number of nucleotide combinations each represented with n number of overlapping nucleotides from among four single nucleotides. For example, an electrical signal for three nucleotides may be measured at once using an electrode having a terminal thickness of about 1.02 nm. A total number of electrical signals corresponding to a nucleotide sequence is 64 ($=4^3$), but only 20 electrical signals ($_4H_3=_6C_3$) are sufficient to represent the nucleotide sequence because the same electrical signal is detected from the same composition regardless of the sequence thereof. Therefore, the nucleotide sequence may be determined by distinguishing only the 20 distinct electrical signals and correlating the signals with a nucleotide sequence. In addition, multiple detections of an electrical signal for each single nucleotide may increase measurement accuracy. For example, if electrical signals can be detected from three nucleotides at once, each nucleotide is subject to the measurement three times, which increases measurement accuracy.

Therefore, with the assumption that an electrical signal measuring device used is able to detect electrical signals for n nucleotides at once, a total number of electric signals measured may be represented as $(n=r-1)!/r1(n-1)!$ ($nHr=n+r-1Cr$).

TABLE 1

| Resolution (No. of nucleotides) | $4^n$ | 4 Hr |
|---|---|---|
| 2 | 16 | 10 |
| 3 | 64 | 20 |
| 4 | 256 | 35 |
| 5 | 1024 | 56 |
| 6 | 4096 | 84 |

Table 1 represents the number of electrical signals with respect to the number of nucleotides (from 2 to 6) subjected to a simultaneous, single measurement (hereinafter, "resolution").

TABLE 2

| Signal level | Nucleotide composition | | |
|---|---|---|---|
| 1 | A | A | A |
| 2 | A | A | C |
| 3 | A | A | G |
| 4 | A | A | T |
| 5 | A | C | C |
| 6 | A | C | G |
| 7 | A | C | T |
| 8 | A | G | G |
| 9 | A | G | T |
| 10 | A | T | T |
| 11 | C | C | C |
| 12 | C | C | G |
| 13 | C | C | T |
| 14 | C | G | G |
| 15 | C | G | T |
| 16 | C | T | T |
| 17 | G | G | G |
| 18 | G | G | T |
| 19 | G | T | T |
| 20 | T | T | T |

Table 2 represents the levels of electrical signals and nucleotide compositions detected with a resolution of 3, using first and second electrodes each having a thickness of about 1.02 nm.

Figure 3:
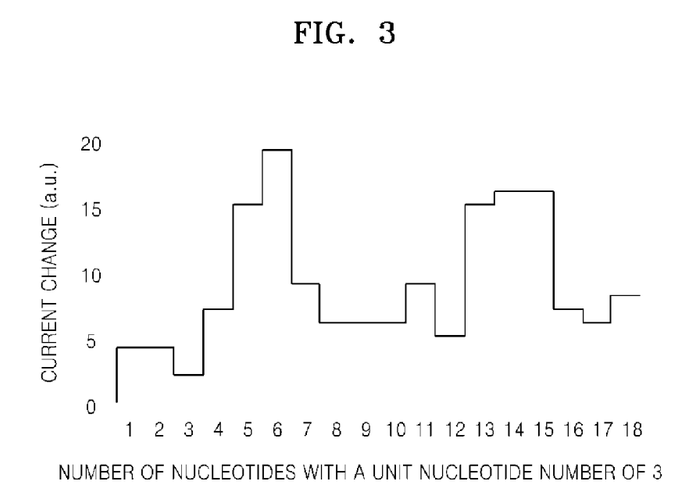
FIG. 3 illustrates changes in current with respect to the number of nucleotides with a unit nucleotide number of 3 when detected from a 20-mer polynucleotide using first and second electrodes with a resolution of 3 nucleotides.

FIG. 3 illustrates changes in current with respect to the number of nucleotides with a unit nucleotide number of 3 when detected from a 20-mer polynucleotide using first and second electrodes. The current may be a tunneling current. The 20-mer polynucleotide may have a nucleotide sequence with SEQ. ID No. 1.

TABLE 3

| Signal level | Nucleotide composition: | | |
|---|---|---|---|
| 4 | A | A | T |
| 4 | A | A | T |
| 2 | A | A | C |
| 7 | A | C | T |
| 15 | C | G | T |
| 19 | G | T | T |
| 9 | A | G | T |
| 7 | A | C | T |
| 7 | A | C | T |
| 7 | A | C | T |
| 9 | A | G | T |
| 6 | A | C | G |
| 15 | C | G | T |
| 16 | C | T | T |
| 16 | C | T | T |
| 7 | A | C | T |
| 6 | A | C | G |
| 8 | A | G | G |

Table 3 represents the levels of electrical signals detected from unit nucleotides each consisting of three nucleotide units of polynucleotide with SEQ. ID No. 1. The levels of electrical signals and nucleotide composition are listed in the order of measurement time.

Figure 4:
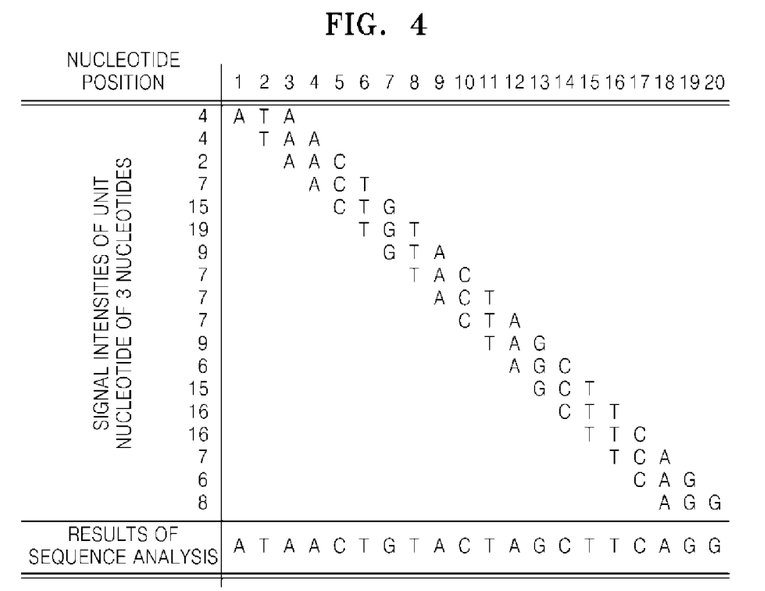
FIG. 4 represents a nucleotide sequence determined based on the levels of the electrical signals of each unit nucleotide of three nucleotides and the nucleotide compositions in Table 3.

FIG. 4 represents a nucleotide sequence determined based on the levels of the electrical signals of each unit nucleotide of three nucleotides and the nucleotide compositions in Table 3. As shown in FIG. 4, the levels of the electrical signals detected from the polynucleotide with 20 nucleotides are 4, 4, 2, 7, 15, 19, 9, 7, 7, 7, 9, 6, 15, 16, 16, 7, 6, and 8 in order, and the nucleotide compositions corresponding to the electrical signal levels are arranged with two overlapping nucleotides, i.e., a single nucleotide gap, between the adjacent nucleotide compositions.

The second and third single nucleotide sequences of the first nucleotide composition (AAT, ATA, or TAA) should overlap with first and second single nucleotide sequences of the second nucleotide composition (AAT, ATA, or TAA), and second and third single nucleotide sequences of the second nucleotide composition (AAT, ATA, or TAA) should overlap with first and second single nucleotide sequences of the third nucleotide composition (AAC, ACA, or CAA). First, second, and third single nucleotide sequences satisfying these requirements are ATA. This may apply to each nucleotide composition from the rest of the nucleotide sequence, thereby determining or estimating the nucleotide sequence with SEQ ID No. 1 based on the data of Table 3.

In some embodiments, a nucleotide sequence of a nucleic acid may be determined or estimated through the above-described processes by measuring a blockade current.

As described above, according to the one or more of the above embodiments of the present invention, using the above-described nucleotide sequence determination or estimation method efficiently determines a nucleotide sequence of a nucleic acid.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of determining or estimating a nucleotide sequence of a nucleic acid, the method comprising:
   translocating the nucleic acid from one end of a nanopore to an opposite end of the nanopore, wherein the nanopore comprises first and second electrodes disposed on an inner wall of the nanopore positioned to apply a voltage across a diameter of the nanopore, and each electrode has a terminal defining at least a portion of the inner wall of the nanopore with a thickness sufficient to detect a signal corresponding to at least two consecutive nucleotides at once;
   measuring an electrical signal between the first and second electrodes as the nucleic acid translocates through the nanopore, wherein the electrical signal is measured with respect to nucleic acid translocating time;
   dividing the measured electrical signal into segments that correspond to a number of nucleotides detected according to the thickness of the electrodes;
   comparing the measured electrical signal of each segment with the electrical signal of a segment from a control to determine the nucleotide composition corresponding to the electrical signal of each segment; and
   determining or estimating the nucleotide sequence of the nucleic acid based on the nucleotide composition of each segment.

2. The method of claim 1, wherein the step of determining or estimating comprises,
   arranging each segment (S) in the order of translocating time as S1, S2, S3, . . . , St, St+1, St+2, St+3, . . .
   providing each potential sequence of each segment (S) from the composition,
   aligning ith-nth sequence of each potential sequence of a segment St with the $1^{st}$-(n−j)th sequence of each potential sequence of a segment St+j, wherein j is an integer from 1 to n−1, wherein i is j+1 and an integer from 2 to n, wherein n refers to the number of nucleotides detected according to the thickness of the electrode,
   determining or estimating the sequence of a segment St as being one more potential sequences that are identical with the aligned $1^{st}$-(n−j)th sequence of each potential sequence of a segment St+j; and
   determining or estimating the nucleotide sequence of the nucleic acid by reading the sequence of each segment in the order of translocating time.

3. The method of claim 2, wherein the first electrode and second electrode are insulated from the substrate using an insulating material.

4. The method of claim 1, wherein the nanopore is part of a nucleotide sequence analysis device comprising:
   a substrate including the nanopore passing through a thickness thereof;
   a voltage source electrically connected to at least one of the first or second electrode; and
   an electrical signal measuring device electrically connected to at least one of the first or second electrode.

5. The method of claim 1, wherein the electrodes have terminals with a thickness greater than about 0.34 nm.

6. The method of claim 1, wherein the electrodes have terminals with a thickness of greater than about 0.34 nm and equivalent to or less than about 0.68 nm, greater than about 0.68 nm and equivalent to or less than about 1.02 nm, greater than about 1.02 nm and equivalent to or less than about 1.36 nm, or greater than about 1.36 nm and equivalent to or less than about 1.70 nm.

7. The method of claim 2, wherein a time interval between St and St+1 is a time corresponding to a single nucleotide translocating time.

8. The method of claim 1, wherein a length of the segment corresponds to the electrical signal from about 2 to about 4 nucleotides.

9. The method of claim 1, wherein the electrical signal is a tunneling current.

10. The method of claim 1, wherein when the nucleotides detected according to the thickness of the electrodes have the same composition, the nucleotides produce the same electrical signal.

11. The method of claim 1, wherein the dividing operation, the comparing operation, and the determining operation are executed by a computer.

12. A method of determining or estimating a nucleotide sequence of a nucleic acid, the method comprising:
- translocating the nucleic acid from one end of a nanopore to an opposite end thereof, wherein the nanopore has a length longer than at least one consecutive nucleotide and able to be blocked in a lengthwise direction by at least two consecutive nucleotides, and a first electrode and a second electrode positioned to apply a voltage across a length of the nanopore;
- applying a voltage across the length of the nanopore, from one end to the opposite end thereof;
- measuring an electrical signal between the first and second electrodes as the nucleic acid translocates through the nanopore with respect to nucleic acid translocating time;
- dividing the measured electrical signal into segments that correspond to a number of nucleotides detected according to the length of the nanopore;
- comparing the measured electrical signal of each segment with the electrical signal of a segment from a control to determine a nucleotide composition corresponding to the electrical signal of each segment; and
- determining or estimating the nucleotide sequence of the nucleic acid based on the nucleotide composition of each segment.

13. The method of claim 12, wherein the step of determining comprises,
- arranging each segment (S) in the order of translocating time as $S_1, S_2, S_3, \ldots, S_t, S_{t+1}, S_{t+2}, S_{t+3}, \ldots$
- providing each potential sequence of each segment (S) from the composition,
- aligning ith-nth sequence of each potential sequence of a segment $S_t$ with the $1^{st}$-(n-j)th sequence of each potential sequence of a segment $S_{t+j}$, wherein j is an integer from 1 to n-1, wherein i is j+1 and an integer from 2 to n, wherein n refers to the number of nucleotides detected according to the length of the nanopore,
- determining or estimating the sequence of a segment $S_t$ as being one more potential sequences that are identical with the aligned $1^{st}$-(n-j)th sequence of each potential sequence of a segment $S_{t+j}$; and
- determining or estimating the nucleotide sequence of the nucleic acid by reading the sequence of each segment in the order of translocating time.

14. The method of claim 12, wherein the nanopore is part of a nucleic acid analysis device comprising:
- a substrate including the nanopore passing through a thickness of the substrate;
- a first electrode and a second electrode positioned to apply a voltage across the length of the nanopore;
- a voltage source electrically connected to the first and second electrodes; and
- an electrical signal measuring device electrically connected to the first and second electrodes.

15. The method of claim 12, wherein the length of the nanopore is longer than about 0.34 nm and equivalent to or less than about 0.68 nm, longer than about 0.68 nm and equivalent to or less than about 1.02 nm, longer than about 1.02 nm and equivalent to or less than about 1.36 nm, or longer than about 1.36 nm and equivalent to or less than about 1.70 nm.

16. The method of claim 12, wherein a time interval between $S_t$ and $S_{t+1}$ is a time corresponding to a single nucleotide translocating time.

17. The method of claim 12, wherein a length of the segment corresponds to the signal from about 2 to about 4 nucleotides.

18. The method of claim 12, wherein measuring the electrical signal comprises measuring a blockade current.

19. The method of claim 12, wherein the dividing operation, the comparing operation, and the determining operation are executed by a computer.

* * * * *